United States Patent [19]

Gorbunov et al.

[11] 4,222,965
[45] Sep. 16, 1980

[54] METHOD OF PRODUCING ACROLEIN

[76] Inventors: Boris N. Gorbunov, prospekt Lenina, 6, kv. 41; Alexandr P. Khardin, ulitsa Krasnopi terskaya, 2, kv. 32, both of Volgograd; Alexandr I. Valdman, ulitsa Sovetskaya 37, kv. 36, Volzhsky, Volgogradskoi oblasti; Vyacheslav K. Rykov, ulitsa Pushkina, 60, kv. 42, Volzhsky, Volgogradskoi oblasti; Stanislav V. Sukhanov, ulitsa Kommunisticheskaya, 30, kv. 15, Volzhsky, Volgogradskoi oblasti, all of U.S.S.R.

[21] Appl. No.: 700,955

[22] Filed: Jun. 29, 1976

Related U.S. Application Data

[63] Continuation of Ser. No. 471,718, May 20, 1974, abandoned.

[30] Foreign Application Priority Data

May 21, 1973 [SU] U.S.S.R. ................................ 1923656

[51] Int. Cl.$^2$ ............................................. C07C 47/22
[52] U.S. Cl. ..................................................... 568/461
[58] Field of Search ..................................... 260/601 R

[56] References Cited

U.S. PATENT DOCUMENTS

| 2,609,387 | 9/1952 | Basdekis et al. | 260/601 R |
| 3,267,132 | 8/1966 | Newsom | 260/465.9 |

FOREIGN PATENT DOCUMENTS 22626 of 1914 United Kingdom ..................... 260/602

OTHER PUBLICATIONS

Schulz et al., Agnew. Chemie, vol. 62, pp. 105–117, (1950).

*Primary Examiner*—Werren B. Lone
*Attorney, Agent, or Firm*—Holman & Stern

[57] ABSTRACT

A method of producing acrolein comprising evaporating acetaldehyde and formaldehyde in the presence of diphenyl-N-nitrosamine taken in an amount of from 0.1 to 3 wt. %. The resultant vapors of said aldehydes are fed for aldol condensation which occurs in a gaseous phase on a catalyst, viz., coarsely porous silica gel promoted by 10 to 12 wt. % sodium silicate at a temperature of from 270° to 300° C. in the presence of diphenyl-N-nitrosamine taken in a quantity of from 0.1 to 3 wt. %. The resultant gas mixture formed at the stage of aldol condensation, containing acrolein, acetaldehyde, formaldehyde and water is cooled to obtain a condensate. Said condensate is subjected to rectification in order to isolate a mixture of acrolein with acetaldehyde and water, and an aqueous formaldehyde solution. Said aqueous formaldehyde solution is concentrated and returned to the aforesaid evaporation stage. Said mixture of acrolein with acetaldehyde and water is subjected to rectification in the presence of diphenyl-N-nitrosamine taken in an amount of from 0.1 to 3 wt. % in order to isolate the end product alongside with acetaldehyde containing from 0.2 to 1.5 wt. % acrolein and returned to the aforesaid evaporation stage. The proposed method makes it possible to avoid completely resinification at the stage of evaporation of aldehydes, to run aldol condensation of acetaldehyde with formaldehyde at a continuous discharge of resins as they form, to carry out rectification of a mixture of acrolein with acetaldehyde and water continuously as well as to substantially increase the purity of the acrolein produced (the acrolein content in the distillate being within 91 to 93 percent).

25 Claims, No Drawings

METHOD OF PRODUCING ACROLEIN

This is a continuation of application Ser. No. 471,718 filed May 20, 1974, now abandoned.

The present invention relates to methods of producing an unsaturated aliphatic aldehyde, viz., acrolein.

Acrolein finds extensive applications in the chemical industry as a valuable intermediate for producing polymers and copolymers incorporating an active carbonyl group, as well as a number of organic compounds such as synthetic glycerol and methionine.

An industrial method of producing acrolein is known in the art (cf. H. Schulz, H. Wagner, Angew. Chem., 62, 105, 1950). The method consists of an aldol condensation of acetaldehyde and formaldehyde in a gaseous phase at from 270° to 330° C. on a catalyst, viz., coarsely porous silica gel promoted by 10 to 12 wt.% sodium silicate, followed by rectification of the reaction mixture. Said method is carried into effect as follows: a vaporizer is charged with preconditioned acetaldehyde and formaldehyde in the form of a mixture of fresh and return aldehydes taken in a definite proportion. Aldehydes are vaporized in the tubular space of a vertical tube type vaporizer with a non-heated still head. Evaporation occurs from the surface of an aqueous layer contained in the still head of the vaporizer. The vapours of the aldehydes at from 125° to 130° C. are superheated to from 270° or 280° C. and fed to the stage of the aldol condensation into the reaction vessel which is in essence a shell-and-tube heat exchanger. The exchanger tubes are filled with the catalyst, viz., coarsely porous silica gel promoted by sodium silicate. Heat for the reaction is obtained by feeding flue gases resulting from natural gas combustion into the exchanger intertube space. A gas mixture resulting from the reaction and containing acrolein, acetaldehyde, formaldehyde and water is deresinated in cyclone separators and coke-packed towers and then condensed in tubular coolers. The obtained condensate is fractionated and the distillate is taken off which is in essence a mixture of acrolein, acetaldehyde and water. The stillage residue in the form of a weak aqueous formaldehyde solution (with a concentration of from 12 to 18 percent) is then subjected to rectification (i.e. concentration of the solution) in order to obtain a 30 to 35 percent formaldehyde solution which is returned to the stage of aldehyde evaporation. The mixture of acrolein with accetaldehyde and water is separated in a plate-type fractionator provided with an outside boiler; from the top of said fractionator, acetaldehyde is taken containing from 0.5 to 1.5 wt.% acrolein and intended to be returned to the stage of aldehyde evaporation, while from the seventeenth plate an 82 to 85 percent solution of acrolein is taken. The isolated acrolein is stabilized with a hydromethanol hydroquinone solution.

In the afore-described method the activity of the catalyst used in the aldol condensation of aldehydes decreases in the process of acrolein synthesis due to its becoming clogged with resins and reaction products. The active life of the catalyst is 30 days on the average involving 5 or 6 catalytic processes. After every reaction run (120 to 150 operating hours) the catalyst activitiy must be regenerated by catalyst oxidation in a steam-and-air stream at 500° to 550° C.

The known method suffers from the disadvantage that a considerable proportion of solid and liquid resin-like products are liable to form at nearly every stage of the process due to the well known tendency of aldehydes for polymerization and polycondensation, especially at high temperatures, which results in blocking the equipment with the products of polymerization and eventually in the process of the synthesis becoming an intermittent one. The resin-like products resulting from aldehyde evaporation are accumulated in the evaporator still and in its tube-pass space, amounting to from 200–250 liters for a five-day operating cycle. At the stage of aldol condensation about 300 to 350 kg of the starting aldehydes are converted into resins per every 1000 kg of acrolein contained in the reaction gases. During separation of a mixture of acrolein with acetaldehyde and water, high-boiling products are accumulated in the fractionator still in amounts of from 1500 to 2000 liters for disposal of which the fractionator is brought out of the production process every 3 to 5 days. Deposition of resins in the evaporator, the aldol condensation reaction vessel and on the catalyst restricts the period of continuous operation of the equipment and requires that all the synthesis process equipment should cease its operation while cleaning the equipment and regenerating the catalyst which takes about 48 hours. The reaction vessel down time, due to the aforesaid causes, makes up 30 percent of the total annual budget of working time. In order to provide a continuous acrolein synthesis process according to the known method, duplicate (standby) process equipment is recommended, if not required.

One more disadvantage inherent in the known method resides also in the relatively low purity of the acrolein obtained whose content in that fraction amounts to as little as 82–85 percent.

It is therefore an object of the present invention to develop such a method of producing acrolein that would make it possible to rule out practically any resinification at the stage of aldehyde evaporation, to effect the aldol condensation of acetaldehyde with formaldehyde with the continuous discharge of the resins as they form, and to carry out fractionation of a mixture of acrolein with acetaldehyde and water on a continuous basis.

It is another object of the present invention to develop such a method that would enable the production of the end product (acrolein) featuring a high degree of purity.

According to said and other objects, the invention resides in that acetaldehyde and formaldehyde are made to evaporate, and said aldehydes are then condensed in the gaseous phase on a catalyst, viz., coarsely porous silica gel promoted by 10 to 12 wt.% sodium silicate, at a temperature of from 270° to 300° C., the thus-formed gas mixture, containing acrolein, acetaldehyde, formaldehyde and water, is cooled to produce a condensate, said condensate is fractionated to isolate a mixture of acrolein with acetaldehyde and water, and an aqueous formaldehyde solution, said formaldehyde solution is being concentrated and returned to the evaporation stage, said mixture of acrolein with acetaldehyde and water is fractionated in order to isolate the end product and acetaldehyde containing from 0.2 to 1.5 wt.% acrolein and intended for return to the evaporation stage.

According to the invention, the aforesaid stages of aldehyde evaporation, aldol condensation and fractionation of a mixture of acrolein with acetaldehyde and water are carried out in the presence of from 0.1 to 3 wt.% diphenyl-N-nitrosamine.

Carrying out all of the aforesaid stages in the presence of diphenyl-N-nitrosamine which is an inhibitor of radical polymerization, results in a considerably reduced resinification and practically rules out completely the clogging of the process equipment at all stages of the proposed method.

The possibility of ruling out resin formation at the stage of evaporation where mixtures of fresh and return aldehydes are used, is accounted for by the fact that in the presence of an inhibitor (diphenyl-N-nitrosamine) the thermal stability of acetaldehyde containing acrolein as an admixture is attained.

The possibility of depositing resin-like products at the stage of aldol condensation is prevented due to the fact that in the presence of said inhibitor, low-molecular resin-like products are formed which are soluble in acrolein and in its concomitant admixtures that wash the resin from the surface of the catalyst, thus extensively prolonging its activity period without regeneration.

The possibility of excluding the resin formation at the stage of rectification of a mixture of acrolein with acetaldehyde and water is due to the fact that in the presence of diphenyl-N-nitrosamine only low-molecular resins are liable to form which are soluble in the admixtures accompanying acrolein, with said resins being disposed during the rectification process along with the stillage residue.

The proposed method reduces the losses of the raw stock, increases the utilization factor of the equipment, and adds much to the purity of the acrolein obtained, the content of which in the distillate is within 91 to 93 percent.

Acetaldehyde and formaldehyde can evaporate, according to the proposed method, either separately or in a mixture. In the latter case, diphenyl-N-nitrosamine is introduced at the evaporation stage as a 0.1 to 2 percent solution in high-boiling organic solvents, and with the mixture of said aldehydes being evaporated from the surface of said solution.

Inasmuch as the formaldehyde fed for evaporation as a mixture of a fresh aldehyde and of a return aldehyde, containing acrolein, is thermally stable and forms no resin-like products, the cause of resin formation in the evaporator is the thermal instability of acetaldehyde which is a mixture of a fresh aldehyde and of a return aldehyde, containing acrolein. This rules out resin formation in the case where there is separate evaporation of both aldehydes, acetaldehyde being evaporated from the surface of a 0.1 to 2 percent diphenyl-N-nitrosamine solution in high-boiling organic solvents, while formaldehyde is evaporated from the surface of water.

Both in conjoint and separate evaporation of the aldehydes it is recommendable to use a 0.3 to 1 percent diphenyl-N-nitrosamine solution in high-boiling organic solvents.

As it has been pointed out hereinbefore, the stage of aldol condensation in the proposed method is carried out likewise in the presence of an inhibitor of radical polymerization, viz., diphenyl-N-nitrosamine. Said inhibitor can be introduced at the stage of aldol condensation by continuously feeding a 0.2 to 3 percent solution thereof in high-boiling organic solvents. Besides, diphenyl-N-nitrosamine can be introduced at the stage of aldol condensation by periodically recirculating a 0.2 to 3 percent solution thereof in high-boiling organic solvents over the catalyst, while the vapours of the starting aldehydes to be fed to said aldol condensation stage are discontinued for the time of inhibitor recirculation. Diphenyl-N-nitrosamine can also be introduced at the stage of aldol condensation by way of a preliminary impregnation of the catalyst with a 0.2 to 3 percent solution thereof in high-boiling organic solvents, followed by drying the catalyst at 110° to 130° C. In the latter case, it is recommended that the diphenyl-N-nitrosamine introduced at said stage of aldol condensation be replenished by periodically recirculating a 0.2 to 3 percent solution thereof in high-boiling organic solvents over the catalyst, and at the same time stopping the feed of the vapours of the starting aldehydes to said aldol condensation stage for the period of time necessary for the inhibitor recirculation.

It is preferable to use at the stage of aldol condensation a 0.3 to 1 percent diphenyl-N-nitrosamine solution in high-boiling organic solvents.

As has been stated hereinabove, the stage of fractionation of a mixture of acrolein with acetaldehyde and water, according to the proposed method, takes place likewise in the presence of diphenyl-N-nitrosamine. Said inhibitor can be introduced at the rectification stage either by preliminarily filling the fractionator still with a 0.1 to 1.5 percent solution thereof in high-boiling organic solvents or by continuously feeding said inhibitor solution to said stage. In both cases rectification of a mixture of acrolein with acetaldehyde and water is accompanied by a continuous discharge of the stillage residue from the fractionator, with said residue being then made to settle down in order to obtain an organic supernatant layer containing diphenyl-N-nitrosamine and high-boiling organic solvents and which is intended to be returned to the rectification stage, and a bottom aqueous layer which is disposed from the system.

It is recommended to use, at the stage of rectification of a mixture of acrolein with acetaldehyde and water, a 0.5 to 1 percent diphenyl-N-nitrosamine solution in high-boiling organic solvents.

In order to obtain the end product of a from 91 to 93 percent concentration and to reduce the acrolein content in the stillage residue to as low as 0.2–1 percent, it is expedient that the rectification of the mixture of acrolein with acetaldehyde and water be carried out at fractionator still temperatures maintained within 95° to 98° C.

Use can be made, according to the proposed method, of high-boiling organic solvents with the inhibitor, of some petroleum distillates, such as a 320° C. boiling-point distillate, absorption oils, e.g., such oils with a boiling point within 230° to 267° C., etc.

Thus, the proposed method as compared to the known method is advantageous in that it makes it possible to rule out the clogging of the process equipment at the stage of aldehyde evaporation, to prevent resin deposition on the catalyst, and to increase the catalytic contact cycle, as well as to effect the stage of rectification of a mixture of acrolein with acetaldehyde and water on a continuous basis, and to add much to the purity of the obtained acrolein whose content in the distillate is as high as from 91 to 93 percent.

The proposed method of producing acrolein is preferably carried into effect as follows:

Acetaldehyde and formaldehyde are fed at a definite space rate of feed, preferentially 190 and 270 l/hr, respectively, each into its particular evaporators. Acetaldehyde fed for evaporation is prepared as a mixture of 1 volume of fresh acetaldehyde with 1.7 to 2 volumes of return acetaldehyde containing from 0.5 to 1.5 wt.% acrolein, while formaldehyde is prepard as a mixture of 1 volume of fresh formalin and 0.9 to 1 volume of return formaldehyde. The still section of the evaporator used for acetaldehyde vaporization is filled with a 0.1 to 2 percent (preferably 0.3 to 1 percent) inhibitor solution in a high-boiling organic solvent to enable acetaldehyde to evaporate from the surface of said solution. Used as high-boiling organic solvents can be, say, ditolylmethane, a 320° C. petroleum distillate, or an absorption oil with a boiling point within 230° to 267° C.

Acetaldehyde vapours having a temperature of from 125° to 130° C., upon leaving the evaporator are passed into the superheater where they are superheated to from 250°-270° C. and then mixed with formaldehyde vapours having a temperature of from 125° to 130° C. and formed in an individual evaporator as the result of formaldehyde evaporation from the surface of water filling the evaporator still.

A mixture of the vapours of acetaldehyde and formaldehyde is fed to the stage of aldol condensation taking place in a reaction vessel which is a shell-and-tube heat exchanger whose tubes are filled with the catalyst, viz., coarsely porous silica gel promoted by 10 to 12 wt.% sodium silicate. The reaction runs in the gaseous phase at 270° to 300° C. in the presence of an inhibitor of radical polymerization, i.e., diphenyl-N-nitrosamine which is continuously introduced into the reaction vessel as a 0.2 to 3 percent (preferably 0.3 to 1 percent) solution in a high-boiling organic solvent. Used as high-boiling organic solvents may be, say, the aforesaid petroleum distillate or an absorption oil.

The gas mixture outflowing from the reaction vessel is deresinated in cyclone separators and coke-packed towers and then cooled to obtain the condensate. Said condensate is fractionated in order to obtain a mixture of acrolein with acetaldehyde and water, and a weak aqueous formaldehyde solution which, upon being concentrated, is returned to the stage of formaldehyde evaporation.

A mixture of acrolein with acetaldehyde and water is fed into a fractionator provided with an outside boiler to separate acetaldehyde containing 0.5 to 1.5 wt.% acrolein and intended to be returned to the stage of acetaldehyde evaporation, and a 91 to 93 percent concentration of acrolein which is then taken off from the system as the end product. Said components are isolated from the mixture on a continuous basis in the presence of a 0.1 to 1.5 percent (preferably 0.5 to 1 percent) solution of diphenyl-N-nitrosamine in a high-boiling organic solvent, with inhibitor being fed into the fractionator still prior to rectification so as to fill the latter to from 60 to 80 percent its full capacity. The temperature inside the still is maintained within 80° to 98° C., preferably 95° to 98° C. During the rectification process, the excess stillage residue is continuously withdrawn and fed for sedimentation into an intermediate vessel (settler). As a result of sedimentation, a supernatant organic layer is formed containing the inhibitor and the high-boiling organic solvent, and which is intended to be returned to the rectification stage, and a bottom aqueous layer which is disposed into a sewage system for chemical wastes. Losses of the high-boiling organic solvent are compensated for by feeding fresh solvent into the settler whose vent pipe communicates with the fractionator.

At the aforesaid stages of acetaldehyde evaporation, the aldol condensation and rectification of a mixture of acrolein with acetaldehyde and water, the amount of the inhibitor is within 0.1 to 3 wt.%.

To promote understanding, given below are some exemplary embodiments of producing acrolein.

EXAMPLE 1

Acetaldehyde and formaldehyde in the form of a mixture of fresh and return aldehydes, taken in a definite proportion, are fed at a space feed rate of 190 and 270 l/hr, respectively, into their individual evaporators which are in essence steam-heated shell-and-tube heat exchangers (F=16 m$^2$). Acetaldehyde fed for evaporation is prepared as a mixture of 1 volume of a fresh product (99.82 percent) and 1.8 volumes of a return product (96.9 percent acetaldehyde and 1.34 percent acrolein). Formaldehyde fed for evaporation is in effect a mixture of 1 volume of a fresh product (34.5 percent) and 0.9 volume of a return product (30.18 percent). The still for the acetaldehyde evaporator is filled with 300 liters of a 0.5 to 1 percent diphenyl-N-nitrosamine solution in a high-boiling organic solvent, viz., a petroleum distillate having a boiling point of 320° C. and a kinematic viscosity $\nu_{100}=7$ cSt.

Acetaldehyde vapours having a temperature of 125° to 130° C., upon leaving the evaporator, are allowed to pass into the superheater which is made as a shell-and-tube heat exchanger (F=12 m$^2$) to be superheated there to from 250°-270° C. and then mixed with the formaldehyde vapours having a temperature of 130° C. resulting from formaldehyde evaporation from the surface of water.

A mixture of the vapours of acetaldehyde and formaldehyde is fed to the reaction vessel for aldol condensation, said vessel being in fact a shell-and-tube heat exchanger (F=129 m$^2$) made of heat-resistant steel, with the tubes of said heat exchanger being filled with 1200 kg of coarsely porous silica gel promoted by 12 wt.% sodium silicate. Concurrently with the vapours of the aldehydes, a solution is introduced continuously into the aldol-condensation reaction vessel consisting of from 0.3 to 0.5 percent diphenyl-N-nitrosamine in a petroleum distillate ($T_{boil.}=320°$ C., $\nu_{100}=7$) which is delivered at a space feed rate of 2.5 to 5 l/hr. The reaction runs at from 270° to 290° C. The catalyst activity period without regeneration equals from 400 to 460 hours with an acrolein content in the resultant gas mixture ranging within 14 to 16 percent.

The gas mixture leaving the reaction vessel is deresinated by passing it through cyclone separators and coke-packed towers, and then dried to obtain the condensate. Said condensate is exposed to rectification to take off a mixture of acrolein with acetaldehyde and water, while the stillage residue, a 13 to 15 percent aqueous formaldehyde solution, is concentrated in order to obtain a 30.18 percent solution which is returned to the stage of formaldehyde evaporation.

The separation of a mixture of acrolein with acetaldehyde and water is carried out in a rectification column having an outside boiler, said column being in effect a 940 mm dia. vertical cylindrical apparatus made of stainless steel and provided with 60 bubble-cap plates. Prior to rectification, the still of the column is filled to 60-percent its full capacity, with a 0.5 to 0.8 percent diphenyl-N-nitrosamine solution in a petroleum distillate ($T_{boil.}=320°$, $\nu_{100}=7$ cSt). Rectification occurs at a space feed rate of a mixture of acrolein with acetaldehyde and water ranging within 1200 to 1500 l/hr, with the temperature of the column top being 21° to 22° C., that of the acrolein take-off plate, 53° to 54° C. and the temperature of the still 96° to 97° C. Acetaldehyde is taken off the column top containing 1.34 wt.% acrolein which is then returned to the acetaldehyde evaporation stage, while from the seventeenth plate acrolein is taken off which makes up 92 to 93 percent of the distillate. The acrolein yield at the rectification stage is 98.7 percent.

The balance excess of the still residue is continuously removed from the bottom line interconnecting the column still with the boiler for sedimentation into an intermediate vessel (settler). As a result of sedimentation there are formed a top (supernatant) organic layer, comprising an inhibitor and a high-boiling organic solvent, viz., a petroleum distillate, and a bottom aqueous layer consisting largely of water with minute admixtures of methanol, crotonaldehyde, low-molecular resin-like products and a high-boiling organic solvent. The supernatant organic layer from the settler is fed into the boiler and then returned into the rectification column, while the bottom aqueous layer is discharged into chemical-waste disposal sewerage. Losses of the high-boiling organic solvent are replenished by feeding a fresh solvent into said settler whose vent pipe is communicated with the column. With such an arrangement for the rectification, assembly the use of an inhibitor enables an uninterrupted rectification process to proceed due to a continuous discharge of the still residue containing low-molecular resinoid products soluble in the admixtures accompanying acrolein, as well as to contribute to a higher purity end product whose content in the distillate equals, as has been stated above, from 92 to 93 percent.

EXAMPLE 2

Acetaldehyde and formaldehyde in the form of a mixture of fresh and return aldehydes, with respective concentrations of 98.1 and 30.5 percent, are fed into an evaporator, viz., a shell-and-tube heat exchanger (F=16 m$^2$) at a space feed rate of 190 and 270 l/hr, respectively. Acetaldehyde fed for evaporation is in fact a mixture of 1 volume of fresh aldehyde (99.9 percent) and 2 volumes of return aldehyde (95.7 percent acetaldehyde and 0.2 percent acrolein), while formaldehyde is made up by 1 volume of fresh aldehyde (35.7 percent) and 1 volume of return aldehyde (30 percent). Said aldehydes are fed under the bottom tube plate of the heat exchanger and are intermixed at the point of their introduction into the evaporator, where said aldehydes are vaporized from the surface of a 1.5 to 2 percent diphenyl-N-nitrosamine solution in an absorption oil ($T_{boil.}$=230° C.) which fills the evaporator still in an amount of 370 liters. Evaporation occurs at 125° to 130° C., with the resultant vapours being superheated to 260°–270° C. and fed into the aldol condensation reaction vessel.

The tube-pass space of the reaction vessel (F=129 m$^2$) is filled with 1200 kg of coarsely porous silica gel promoted by 10 wt.% sodium silicate. Concurrently with the superheated aldehyde vapours, introduced continuously into the reaction vessel is a from 2.5 to 3 percent diphenyl-N-nitrosamine solution in an absorption oil ($T_{boil}$=230°) which is fed at a space feed rate of from 1.5 to 2 l/hr. The reaction of aldol condensation occurs at from 280° to 300° C., with the catalyst activity period amounting to from 370–420 hours without regeneration and the acrolein content in the resultant gas mixture being from 13 to 15 percent.

The gas mixture escaping from the reaction vessel is deresinated and cooled in order to obtain a condensate. Said condensate is fractionated so as to remove a mixture of acrolein with acetaldehyde and water, while the still residue in the form of a 16 to 18 percent aqueous formaldehyde solution is concentrated in order to obtain a 30-percent solution which is returned to the stage of aldehyde evaporation.

The separation of a mixture of acrolein with acetaldehyde and water is carried out in a 940 mm diameter fractionator with an outside boiler. Rectification occurs at a space feed rate for the mixture of acrolein with acetaldehyde and water of from 1100–1300 l/hr, with said mixture being fed onto the column continuously and concurrently with a 0.1 to 0.3 percent diphenyl-N-nitrosamine solution in an absorption oil ($T_{boil.}$=230° C.), at a rate of from 0.3 to 0.5 weight percent of the inhibitor per total weight of the inhibited mixture. The temperature of the still is kept at 80° to 85° C. Acetaldehyde is taken off the column top containing 0.2 wt.% acrolein which is then returned to the stage of aldehyde evaporation, while from the seventeenth plate acrolein is taken off with a concentration of 91 to 92 percent. The yield of acrolein at the rectification stage is 99.2 percent. The stillage residue is discharged from the fractionator in a way similar to that described in Example 1.

EXAMPLE 3

Aldehydes are evaporated as described in Example 1 with the sole exception that fed for the evaporation is acetaldehyde which is in effect a mixture of 1 volume of fresh aldehyde (99.87 percent) and 1.75 volumes of return aldehyde (94.5 percent acetaldehyde, 1.5 percent acrolein), where acetaldehyde is evaporated from the surface of a 0.1 to 0.3 diphenyl-N-nitrosamine solution in a petroleum distillate ($T_{boil.}$=320° C., $\nu_{100}$=7 cSt).

The vapours of acetaldehyde are superheated to 270° C., mixed with the vapours of formaldehyde having a temperature of 130° C. and resulting from its evaporation from the surface of water, and the thus-formed mixture of the vapours is fed into the reaction vessel for aldol condensation.

The aldol condensation is carried out as in Example 1 with the exception that the concentration of the diphenyl-N-nitrosamine solution in a petroleum distillate fed into the reaction vessel is within 0.2 to 0.4 percent.

The gas mixture coming out of the reaction vessel is deresinated and cooled, and the resultant condensate is fractionated as described in Example 1 in order to obtain acrolein with a concentration of 91.8 percent, with the yield of acrolein at the rectification stage being within 98 to 99.5 percent.

EXAMPLE 4

The evaporation of the aldehydes and the feeding of the resultant vapours to the stage of aldol condensation are carried out similarly to Example 1.

The reaction of aldol condensation is carried out at 280° to 295° C. in a reaction vessel (F=129 m$^2$) whose tube-pass space accommodates 400 kg of a coarsely porous silica gel promoted by sodium silicate (11 wt.%) and preliminarily (prior to being charged into the reaction vessel) impregnated with from 900 to 1200 liters of a 0.2 to 0.4 diphenyl-N-nitrosamine solution in an absorption oil ($T_{boil}$=267° C.) and then dried at from 120° to 130° C. Placed above the inhibited catalyst are 800 kg of coarsely porous silica gel promoted by 11 wt.% of sodium silicate but not impregnated with the inhibitor solution. The catalyst activity time without regeneration is from 300 to 320 hours, with the acrolein content in the thus-formed gas mixture being within 13 to 15 percent.

The subsequent deresination of the gas mixture escaping from the reaction vessel, its cooling, and the fractionation of the resulting condensate into a weak aqueous formaldehyde solution and a mixture of acrolein with acetaldehyde and water, are carried out similarly to Example 1.

The separation of a mixture of acrolein with acetaldehyde and water is performed as in Example 1 with the exception that the fractionator still is filled, prior to the rectification process, from 55 to 65 percent its full capacity, with a 1 to 1.5 diphenyl-N-nitrosamine solution in a petroleum distillate. As a result, acrolein with a concentration of 92 percent is produced, with its yield at the rectification stage being 99.3 percent.

EXAMPLE 5

The evaporation of the aldehydes and the feeding of the resulting vapours to the stage of aldol condensation are carried out as described in Example 1 with the exception that fed for evaporation is acetaldehyde which is a mixture of 1 volume of fresh aldehyde (99.82 percent) and 1.9 volumes of return aldehyde (95.4 percent acetaldehyde and 0.7 percent acrolein), and acetaldehyde is evaporated from the surface of a 0.3 to 0.5 percent diphenyl-N-nitrosamine solution in an absorption oil ($T_{boil.}=230°$ C.).

The reaction of aldol condensation occurs similarly to Example 4 with the sole exception that the reaction vessel tube-pass space ($F=129$ m$^2$) accommodates 1200 kg of coarsely porous silica gel promoted by sodium silicate (12 wt.%) and preliminarily impregnated with from 1000 to 1200 liters of a 2.5 to 3 percent diphenyl-N-nitrosamine solution in an absorption oil ($T_{boil.}=230°$ C.) and then dried at from 110° to 120° C. The catalyst activity period without regeneration is within 380 to 420 hours, with the acrolein content in the thus-formed gas mixture being within 15 to 17 percent.

The gas mixture passing from the reaction vessel is deresinated, cooled to produce a condensate and the latter is fractionated into a mixture of acrolein with acetaldehyde and water, and weak formaldehyde solution (16 to 18 percent) in a way similar to that described in Example 1.

The separation of a mixture of acrolein with acetaldehyde and water is carried out as described in Example 1, with the resultant acetaldehyde (95.4 percent acetaldehyde and 0.7 percent acrolein) then being returned to the evaporation stage, and the acrolein has a concentration of 98.2 percent. The yield of acrolein at the rectification stage equals 99.5 percent.

EXAMPLE 6

The evaporation of the aldehydes and the feeding of the resultant vapours to the aldol condensation stage are carried out similarly to Example 1.

The reaction of the aldol condensation occurs at from 270° to 290° C. in a reaction vessel ($F=129$ m$^2$) the tubes of which are filled with 1200 kg of a coarsely porous silica gel promoted by 12 wt.% sodium silicate. Before feeding aldehyde vapours into the reaction vessel, from 800 to 1000 liters of a 0.7 to 1 percent diphenyl-N-nitrosamine solution in a petroleum distillate ($T_{boil.}=320°$ C.) are recirculated over the catalyst.

After from 3 to 5 hours the inhibitor solution ceases to be recirculated, and the aldehyde vapours are fed from the evaporation stage. The catalyst activity time without regeneration is within 360 to 400 hours, the acrolein content in the thus-formed gas mixture equalling 14 to 16 percent.

Subsequent deresination of the gas mixture escaping from the reaction vessel, its, cooling and the condensate fractionation so as to obtain a mixture of acrolein with acetaldehyde and water are carried out as described in Example 1.

The mixture of acrolein with acetaldehyde and water is separated as described in Example 1 with the temperature of the fractionator still being maintained within 95° to 97° C. As a result, a 93-percent concentration acrolein is produced, with its yield at the rectification stage being equal to 99.3 percent.

EXAMPLE 7

The evaporation of the aldehydes and feeding of the resultant vapours to the aldol condensation stage are carried out as described in Example 1.

The reaction of aldol condensation is conducted at from 280° to 300° C. in a reaction vessel ($F=129$ m$^2$) whose tube-pass space accommodates 1200 kg of a coarsely porous silica gel promoted by sodium silicate (12 wt.%) and which is preliminarily impregnated with from 900 to 1100 liters of a from 0.5 to 0.8 percent diphenyl-N-nitrosamine solution in a petroleum distillate ($T_{boil.}=320°$ C.; $v_{100}=7$ cSt) and then dried at 120° to 130° C. The reaction of the aldol condensation takes from 200 to 240 hours to occur, after which time the aldehyde vapours are suspended from being fed into the reaction vessel, and from 800 to 1000 liters of a 0.5 to 0.8 percent diphenyl-N-nitrosamine solution in a petroleum distillate are recirculated over the catalyst for about 5 hours. Then the flow of aldehyde vapours is restarted into the reaction vessel and the aldol condensation reaction runs for another 200 to 240-hour period. The catalyst activity period without regeneration is within 720 to 750 hours.

The gas mixture leaving the reaction vessel is deresinated and cooled, and the condensate is fractionated to obtain a mixture of acrolein with acetaldehyde and water similarly to Example 1.

Separation of said mixture of acrolein with acetaldehyde and water is carried out as described in Example 1, with the fractionator still temperature being maintained within 85° to 87° C. As a result, a 92.5-percent concentration acrolein is obtained.

EXAMPLE 8

Evaporation of the aldehydes and the feeding of the resultant vapours to the stage of aldol condensation are carried out as described in Example 1.

The reaction of aldol condensation occurs according to Example 7, with the sole exception that the concentration of the diphenyl-N-nitrosamine solution in a petroleum distillate recirculated over the catalyst is within 0.2 to 0.5 percent.

Subsequent deresination of the gas mixture passing from the reaction vessel, its cooling, and the fractionation of the resultant condensate to obtain a mixture of acrolein with acetaldehyde and water, and the isolation of acrolein having a concentration of 92 to 92.5 percent from said mixture is carried out in a way similar to that described in Example 1.

What is claimed is:

1. A method of producing acrolein, comprising evaporating acetaldehyde and formaldehyde in the presence of from 0.1 to 3 wt.% diphenyl-N-nitrosamine; forming aldols from the resultant vapours of the aldehydes in an aldol condensation reactor which is carried out in the gaseous phase on a catalyst consisting of coarse porous silica gel enhanced by 10-12 wt.% sodium silicate at 270°-300° C. in the presence of 0.1 to 3 wt.% diphenyl-N-nitrosamine; cooling the gas mixture resulting at the stage of aldol condensation and which contains acrolein, acetaldehyde, formaldehyde and water in order to produce a condensate; subjecting said condensate to rectification to isolate a mixture of acrolein with acetaldehyde and water, and an aqueous formaldehyde solution; concentrating said aqueous formaldehyde solution and returning same to the aforesaid evaporation stage; subjecting said mixture of acrolein with acetaldehyde and water to rectification in the presence of from 0.1 to 3 wt.% diphenyl-N-nitrosamine to isolate the end product and acetaldehyde containing from 0.2 to 1.5 wt.% acrolein, and returning the acetaldehyde containing from 0.2° to 1.5° wt.% acrolein to the aforesaid evaporation stage.

2. The method as claimed in claim 1, wherein said diphenyl-N-nitrosamine is introduced at the stage of evaporation of the aldehydes as a 0.1 to 2 percent solution thereof in high-boiling organic solvents, while evaporating the misture of said aldehydes from the surface of said solution.

3. The method as claimed in claim 2, wherein a 0.3 to 1 percent diphenyl-N-nitrosamine solution in high-boiling organic solvents is used.

4. The method aas claimed in claim 2, wherein the high-boiling organic solvents are selected from the group consisting of a 320° C. petroleum distillate, and an absorption oil having a boiling point from 230° to 267° C.

5. The method as claimed in claim 1, comprising evaporating acetaldehyde and formaldehyde separately, with diphenyl-N-nitrosamine being introduced at the stage of acetaldehyde evaporation as a 0.1 to 2 percent solution thereof in high-boiling organic solvents, and evaporating acetaldehyde from the surface of said solution, while evaporating formaldehyde from the surface of the water.

6. The method as claimed in claim 5, wherein a 0.3 to 1 percent diphenyl-N-nitrosamine solution in high-boiling organic solvents is used.

7. The method as claimed in claim 5, wherein said high-boiling organic solvents are selected from the group consisting of a 320° C. petroleum distillate and an absorption oil having a boiling point from 230° to 267° C.

8. The method as claimed in claim 1, wherein diphenyl-N-nitrosamine is introduced at the stage of aldol condensation by being continuously fed as a 0.2 to 3 percent solution thereof in high-boiling organic solvents.

9. The method as claimed in claim 8, wherein a 0.3 to 1 percent diphenyl-N-nitrosamine solution in high-boiling organic solvents is used.

10. The method as claimed in claim 8, wherein the high-boiling organic solvents are selected from the group consisting of a 320° C. petroleum distillate, and an absorption oil having a boiling point within 230° to 267° C.

11. The method as claimed in claim 1, wherein diphenyl-N-nitrosamine is introduced at the stage of aldol condensation by periodical recirculation of a 0.2 to 3 percent solution thereof in high-boiling organic solvents over the catalyst, while the feeding of vapours of the starting aldehydes is discontinued to said aldol condensation stage for the time necessary for said recirculation.

12. The method as claimed in claim 11, wherein a 0.3 to 1 percent diphenyl-N-nitrosamine solution in high-boiling organic solvents is used.

13. The method as claimed in claim 11, wherein the high-boiling organic solvents are selected from the group consisting of a 320° C. petroleum distillate, and an absorption oil having a boiling point within 230° to 267° C.

14. The method as claimed in claim 1, wherein diphenyl-N-nitrosamine is introduced at the stage of aldol condensation by preliminarily impregnation the catalyst with a 0.2 to 3 percent diphenyl-N-nitrosamine solution in high-boiling organic solvents followed by catalyst drying at 110° to 130° C.

15. The method as claimed in claim 14, wherein a 0.3 to 1 percent diphenyl-N-nitrosamine solution in high-boiling organic solvents is used.

16. The method as claimed in claim 14, wherein the high-boiling organic solvents are selected from the group consisting of a 320° C. petroleum distillate, and an absorption oil having a boiling point within 230° to 267° C.

17. The method as claimed in claim 14, wherein the amount of diphenyl-N-nitrosamine engaged at the stage of aldol condensation is replenished by periodically recirculating a 0.2 to 3 percent solution thereof in high-boiling organic solvents over the catalyst, while the vapours of the starting aldehydes feed to said aldol condensation stage is discontinued for the time necessary for said recirculation.

18. The method as claimed in claim 1, wherein diphenyl-N-nitrosamine is introduced at the stage of rectification of a mixture of acrolein with acetaldehyde and water by preliminarily filling the fractionator still with a 0.1 to 1.5 percent diphenyl-N-nitrosamine solution in high-boiling organic solvents.

19. The method as claimed in claim 18, wherein a 0.5 to 1 percent diphenyl-N-nitrosamine solution in high-boiling organic solvents is used.

20. The method as claimed in claim 18, wherein the high-boiling organic solvents are selected from the group consisting of a 320° C. petroleum distillate, and an absorption oil having a boiling point within 230° to 267° C.

21. The method as claimed in claim 18, wherein rectification of the mixture of acrolein with acetaldehyde and water occurs at a still temperature ranging within 95° to 98° C.

22. The method as claimed in claim 1, wherein diphenyl-N-nitrosamine is introduced at the stage of rectification of the mixture of acrolein with acetaldehyde and water by being continuously fed as a 0.1 to 1.5 percent solution in high-boiling organic solvents.

23. The method as claimed in claim 22, wherein a 0.5 to 1 percent diphenyl-N-nitrosamine solution in high-boiling organic solvents is used.

24. The method as claimed in claim 22, wherein the high-boiling organic solvents are selected from the group consisting of a 320° C. petroleum distillate, and an absorption oil having a boiling point within 230° to 267° C.

25. The method as claimed in claim 22, wherein rectification of the mixture of acrolein with acetaldehyde and water occurs at a still temperature ranging within 95° to 98° C.

* * * * *